US007713935B2

(12) United States Patent
Kelly

(10) Patent No.: US 7,713,935 B2
(45) Date of Patent: May 11, 2010

(54) COMPOUNDS THAT MODULATE TRH ACTIONS

(75) Inventor: Julie Kelly, Dublin (IE)

(73) Assignee: The Provost, Fellows and Scholars of The College of The Holy and Undivided Trinity of Queen Elizabeth Near Dublin, Dublin (IE)

(*) Notice: Subject to any disclaimer, the term of this patent is extended or adjusted under 35 U.S.C. 154(b) by 275 days.

(21) Appl. No.: 11/576,228

(22) PCT Filed: Oct. 3, 2005

(86) PCT No.: PCT/IE2005/000110

§ 371 (c)(1),
(2), (4) Date: Jul. 25, 2007

(87) PCT Pub. No.: WO2006/038206

PCT Pub. Date: Apr. 13, 2006

(65) Prior Publication Data

US 2007/0265202 A1 Nov. 15, 2007

(30) Foreign Application Priority Data

Oct. 1, 2004 (IE) .................... 2004/0669

(51) Int. Cl.
*A61K 38/16* (2006.01)
*A01N 43/74* (2006.01)
(52) U.S. Cl. .................... 514/13; 514/43; 514/18; 530/324
(58) Field of Classification Search ........ None
See application file for complete search history.

(56) References Cited

U.S. PATENT DOCUMENTS

| 4,587,233 | A | 5/1986 | Barchas et al. ........ 514/15 |
| 4,906,614 | A | 3/1990 | Giertz et al. ........ 514/18 |
| 5,112,804 | A | 5/1992 | Kowarski ........ 514/3 |
| 5,244,884 | A | 9/1993 | Spatola et al. ........ 514/18 |
| 5,428,006 | A | 6/1995 | Bechgaard et al. ........ 514/3 |
| 5,686,420 | A | 11/1997 | Faden ........ 514/18 |
| 5,693,608 | A | 12/1997 | Bechgaard et al. ........ 514/2 |
| 5,804,212 | A | 9/1998 | Illum ........ 424/434 |
| 6,475,989 | B1 | 11/2002 | Sattin et al. ........ 514/18 |
| 6,491,939 | B2 | 12/2002 | Kubek ........ 424/423 |
| 6,524,557 | B1 | 2/2003 | Backstrom et al. ........ 424/46 |
| 6,703,366 | B2 | 3/2004 | Jackowski et al. ........ 514/13 |
| 2002/0004062 | A1 | 1/2002 | Kubek ........ 718/107 |
| 2003/0166944 | A1* | 9/2003 | Kelly ........ 548/180 |

FOREIGN PATENT DOCUMENTS

WO    WO 01/60843    8/2001

OTHER PUBLICATIONS

Wilk, 1989, Neurochem. Int., 15, 81-89.*

Charli et al., "Pyroglutamyl peptidase II inhibition specifically increases recovery of TRH released from rat brain slices," *Neuropeptides*, 14:191-196, 1989.
Elmore et al., "Further characterization of the substrate specificity of a TRH hydrolysing pyroglutamate aminopeptidase from guinea-pig brain," *Neuropeptides*, 15:31-36, 1990.
Faden and Salzman, "Pharmacological strategies in CNS trauma," *Trends Pharmacol. Sci.*, 13:29-35, 1992.
Fischer, "The design, synthesis and application of stereochemical and directional peptide isomers: a critical review," *Curr. Protein Pept. Sci.*, 4:339-356, 2003.
Gershengorn and Osman, "Molecular and cellular biology of thyrotropin-releasing hormone receptors," *Physiol. Rev.*, 76:175-191, 1996.
Horita, "An update on the CNS actions of TRH and its analogs," *Life Sci.*, 62:1443-1448, 1998.
Hruby, "Designing peptide receptor agonists and antagonists," *Nat. Rev. Drug Discov.*, 1:847-858, 2002.
Karle et al., "Crystal structure of a hydrophobic 19-residue peptide helix containing three centrally located D amino acids," *Proc. Natl. Acad. Sci. USA*, 100:13946-13951, 2003.
Kelly et al., "British Pharmacological Society Jun. 2000," *Br. J. Pharmacol.*, 133:187P, 2000.
Kelly et al., "Kinetic investigation of the specificity of porcine brain thyrotropin-releasing hormone-degrading ectoenzyme for thyrotropin-releasing hormone-like peptides," *J. Biol. Chem.*, 275:16746-16751, 2000.
Kelly et al., "Pharmacologically distinct binding sites in rat brain for [3H]thyrotropin-releasing hormone (TRH) and [3H][3-methyl-histidine(2)]TRH," *Biochem. Pharmacol.*, 63:2197-2206, 2002.
Kelly et al., "Structure-activity studies with high-affinity inhibitors of pyroglutamyl-peptidase II," *Biochem. J*, 389:569-576, 2005.
Kelly, "Thyrotropin-releasing hormone: basis and potential for its therapeutic use," *Essays Biochem.*, 30:133-149, 1995.
Leng et al., "D-amino acid substitution of residues 32 to 46 of the glycoprotein hormone common alpha-subunit: development of a synthetic glycoprotein hormone antagonist," *Pept. Res.*, 9:188-194, 1996.
Luo et al., "Thyrotropin releasing hormone (TRH) in the hippocampus of Alzheimer patients," *J. Alzheimers Dis.*, 4:97-103, 2002.
Magdolen et al., "Cyclo19,31[D-Cys19]-uPA19-31 is a potent competitive antagonist of the interaction of urokinase-type plasminogen activator with its receptor (CD87)," *Biol. Chem.*, 382:1197-1205, 2001.
Metcalf, "The neuropharmacology of TRH analogs," *Thyrotropin-Releasing Horm.*, Raven Publisher (Griffiths and Bennett, eds.), New York, 315-326, 1983 (Database CA, Database Accession No. 1983:28331).

(Continued)

*Primary Examiner*—Andrew D Kosar
*Assistant Examiner*—Satyanarayana R Gudibande
(74) *Attorney, Agent, or Firm*—Fulbright & Jaworski L.L.P.

(57) ABSTRACT

The invention relates to compounds that inhibit thyrotropin-releasing hormone (TRH) degrading ectoenzyme and/or enhance, and/or mimic the biological actions of TRH. The compounds find therapeutic application, particularly in conditions involving neuronal cell injury and disturbances in neurobiological function.

23 Claims, 9 Drawing Sheets

OTHER PUBLICATIONS

O'Cuinn et al., "Degradation of thyrotropin-releasing hormone and luteinising hormone-releasing hormone by enzymes of brain tissue," *J. Neurochem.*, 54:1-13, 1990.

Pascual et al., "Purification of a specific inhibitor of pyroglutamyl aminopeptidase II from the marine annelide *Hermodice carunculata*. In vivo effects in rodent brain," *Int. J. Biochem. Cell Biol.*, 36:138-152, 2004.

PCT International Search Report, dated May 24, 2006.

Sato et al., "Synthesis and in vitro bioactivity of human growth hormone-releasing factor analogs substituted with a single D-amino acid," *Biochem. Biophys. Res. Commun.*, 149:531-537, 1987.

Sharif, "Quantitative autoradiography of TRH receptors in discrete brain regions of different mammalian species," *Ann. NY Acad Sci.*, 553:147-175, 1989.

Wilk and Wilk, "Pyroglutamyl Peptidase II, a Thyrotropin Releasing Hormone Degrading Enzyme: Purification and Specificity Studies of the Rabbit Brain Enzyme," *Neurochem. Int.*, 15:81-89, 1989.

* cited by examiner

COMPOUNDS THAT MODULATE TRH ACTIONS

CROSS REFERENCE TO RELATED APPLICATIONS

The present application is a national phase application under 35 U.S.C. 371 of International Application No. PCT/IE2005/000110, filed 3 Oct. 2005, which claims the benefit of Ireland Application No. 2004/0669 filed 1 Oct. 2004. The entire text of these applications are incorporated by reference.

FIELD OF THE INVENTION

The present invention relates to novel peptides and uses thereof. In particular, it relates to compounds that inhibit thyrotropin-releasing hormone (TRH)-degrading ectoenzyme (TRH-DE) (EC 3.4.19.6), also known as pyroglutamyl aminopeptidase II (PAP-II, PP-II), and/or enhance, and/or mimic the biological actions of TRH. As a result, compounds of the invention find potential therapeutic application in the field of medicine, particularly, but not limited to, conditions involving neuronal cell injury and disturbances in neurobiological Function. They also have application as tools for studying the biological functions of TRH, TRH-DE and TRH receptors.

BACKGROUND OF THE INVENTION

TRH has the structure

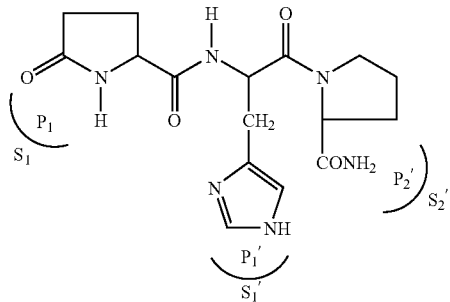

The nomenclature of Schechter and Berger is used to describe the positions of the peptide substrate residues (P) relative to the scissile $P_1$—$P_1'$ bond and the corresponding subsets (S) in the active site of the enzyme. In other literature, the right portion of the molecule is called the "prolineamide" or "C-terminal" portion; the centre portion of the molecule is called the "histidyl" portion; and the left portion of the molecule is called the "pyroglutamyl", or "N-terminal" portion.

Thyrotropin-releasing hormone (TRH) (pyroglutamyl-histidyl-prolineamide, Glp-His-ProNH$_2$) is a naturally occurring neuroactive peptide with multiple actions in the central nervous system (CNS) that have been shown to be beneficial in the treatment of CNS disorders, including brain and spinal injury, stroke, epilepsy and spinocerebellar degeneration. While mechanisms underlying the therapeutic actions of TRH are not fully understood, it is recognized by the art that TRH has substantial beneficial effects due in part to its action in mitigating the secondary neuronal cell damage caused by a sequence of biochemical reactions triggered by the primary injury. This same sequence of reactions has been found to occur in both acute and chronic neurodegeneration and drugs capable of disrupting this sequence have potentially broad application as neuroprotectants. It is becoming evident that those targeting multiple components of the sequence may offer therapeutic advantages over pharmacological interventions targeted at single components. Notably TRH has been shown to antagonize the actions of multiple constituents of the sequence and also improve critical biochemical functions impaired by CNS trauma such as cell bioenergetics. TRH's neurotrophic actions may also be beneficial for restoring loss of function associated with neurodegeneration.

Recent literature highlights a growing recognition of the breadth of TRH functions and the potential widespread clinical applicability of this remarkable peptide. For example, it has been recognized recently that TRH may function as a core homeostatic regulator within four integrated CNS systems and as such may have extensive involvement and therapeutic application in human illnesses associated with disturbances in neurobiological function, including conditions as diverse as jetlag, obesity and depression. Other research strongly indicates a role for TRH in the physiology and treatment of mood disorders and epilepsy. In a recent paper (Luo et al., 2002) it was suggested that TRH might function as an endogenous neuroprotectant and that the low levels of TRH found in the hippocampus of Alzheimer's patients may possibly contribute to the pathogenesis of this disorder. In relation to epilepsy, the art shows that TRH is efficacious in treating patients with intractable epilepsy. In addition, the art indicates that the brain naturally releases TRH in response to seizures and that endogenous TRH has an anticonvulsant function in brain and plays a homeostatic role in reducing the potentially damaging effects of epilepsy.

The art shows that in human clinical trials TRH has a large therapeutic window and is well tolerated. The clinical utility of TRH is, however, severely limited by its susceptibility to enzymic degradation, which significantly reduces TRH bioavailability and duration of action (Kelly, 1995). This is reflected in a disappointing performance produced by native TRH in clinical trials. The short half-life of TRH, arising from enzymic degradation, is also a serious impediment to further investigation of the functions of TRH.

As a means to overcome the susceptibility of TRH to metabolism the art has, to date, concentrated largely on the development of improved delivery systems and degradation-stabilized TRH analogs, which target TRH receptors and act as TRH mimetics. U.S. Pat. No. 5,244,884 relates to thionated analogs of TRH type compounds, which selectively bind to TRH receptor binding sites in animals with high affinity and have potentially pharmacological advantages over TRH in treating pathological conditions in which the effects of TRH have been shown to be beneficial. U.S. Pat. Nos. 5,112,804, 5,428,006 5,693,608, 5,804,212, 6,491,939, 6,524,557 describe methods for administrating a therapeutically effective amount of biologically active substances, including TRH. U.S. Pat. No. 5,686,420 describes a series of novel TRH analogs wherein the C-terminal prolineamide moiety has been preserved, the N-terminal moiety comprises one of five different ring structures and the histidyl moiety is substituted with $CF_3$, $NO_2$ or a halogen and use of these analogs in the treatment of neurological disorders. US patent application 20020004062 describes methods and compositions for providing prolonged release of therapeutic agents, including TRH. U.S. Pat. No. 6,475,989 relates to peptides with the general formula Glp-X-ProNH$_2$ and their potential therapeutic application. Thus far, one degradation-stabilized analog has been approved for therapeutic use in humans; this was launched by Tanabe Seiyaku Co., Ltd., in 2000 for the treatment of spinocerebellar degeneration, an orphan drug designated disorder. In contrast to TRH analogs described in U.S.

Pat. No. 5,686,420 and US patent application 20020004062, the C-terminal prolineamide moiety that is found in TRH and TRH-like peptides has not been preserved in compounds described in the present invention, described herein.

The art shows that many degradation-stabilised analogs that act as TRH mimetics contain modifications to the N-terminal pyroglutamyl residue of TRH (Kelly 1995, Horita 1998, Faden & Salzman 1992). For example, the N-terminal pyroglutamyl residue of TRH has been replaced by a 6-membered ring (e.g. TA-0910 i.e. Ceredist, CG3509, CG3703), a different 5-membered ring (e.g. DN1417, JTP2942) and a 4-membered ring (e.g. YM14673). Such analogs have been shown by the art to mimic the central actions of TRH, despite displaying reduced affinity for TRH receptors.

The following are a selection of known TRH analogs:

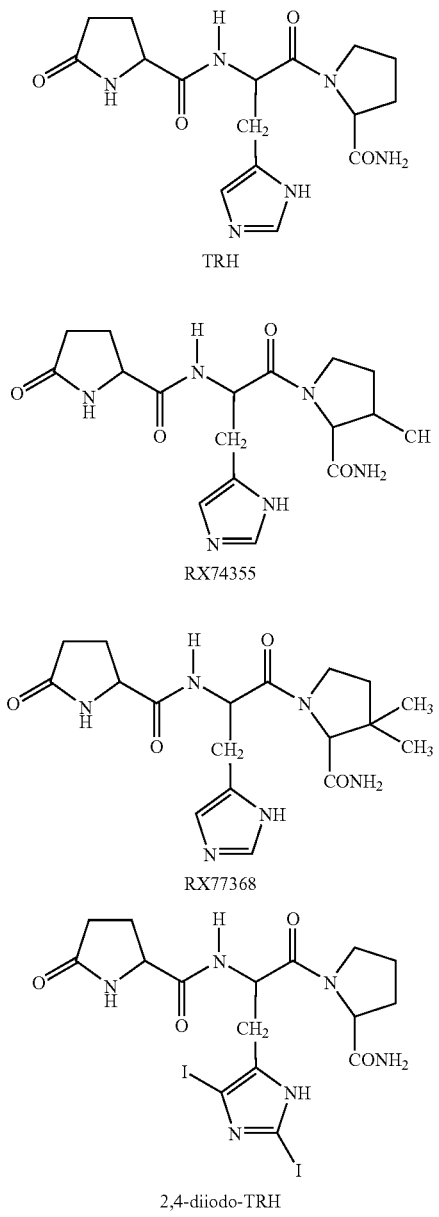

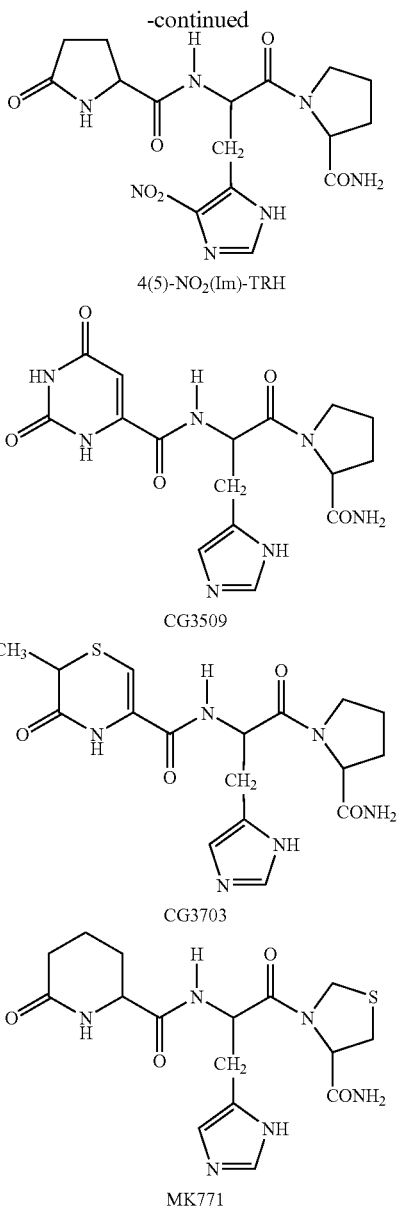

An alternative approach to facilitate the clinical use of TRH is to protect it from degradation by inhibiting its enzymic degradation. TRH-degrading ectoenzyme (TRH-DE) (EC 3.4.19.6), also known as pyroglutamyl aminopeptidase II (PAP-II, PP-II) is recognized by the art to be the enzyme responsible for degrading extracellular TRH. Thus, TRH-DE is an attractive therapeutic target because of the potential offered by TRH-DE inhibitors to enhance the therapeutic effects of TRH. TRH-DE catalyzes the removal of the N-terminal pyroglutamyl group from TRH and is located on the surface of neuronal cells. A soluble form of the enzyme, known as thryoliberinase, is present in serum. TRH-DE appears to be a rare example of a neuropeptide-specific peptidase in that it displays absolute functional specificity for TRH. Furthermore, TRH is not degraded by any other enzymes that are in a position to affect TRH signaling. Hence, the modulation of TRH-DE activity should, in principle, amplify TRH effects exclusively. The special relationship between TRH-DE and TRH should ensure that only the biological actions of TRH are amplified and thus, lead to minimal side effects.

To date, there is no crystal structure or homology model for TRH-DE on which to base the rational design of active site directed inhibitors. Nevertheless, through research carried out by the inventor named herein novel, potent. competitive inhibitors of TRH-DE have been identified (Kelly et al. 2000a, 2000b, U.S. Pat. App. 20030166944). Prior to this, few TRH-DE inhibitors had been reported—the most potent of these was N-[1-carboxy-2-phenylethyl]N-imidazole benzyl histidyl-β-naphthylamide ($K_i$ of 8 mM) (Charli et al., 1989). A recent paper by Pascual et al., (2004) has described the isolation of a TRH-DE inhibitory activity from a marine invertebrate. However, the type of inhibition has not been defined, its molecular structure is not yet known, nor is it certain that inhibition is due to a single chemical entity.

The art indicates that actions of peptides, such as TRH, are mediated by specific receptors. Two TRH receptor subtypes have been described thus far: TRH receptor 1 (TRHR1) and TRH receptor 2 (TRHR2). These receptors have distinct amino acid sequences and distribution patterns, but both display a similar high-affinity for [$^3$H][3-Me-His$^2$]TRH. TRHR1 is highly conserved between species, including human. Unlike TRHR1, TRHR2 has not been identified in humans. In rat TRHR2 expression is restricted to the CNS. This contrasts with TRHR1, which displays very limited mRNA expression in the CNS. The regional distribution of TRHR2 mRNA has been found to be consistent with the possibility that this TRH receptor is involved in mediating the higher cognitive functions of TRH, as well as its effects on arousal, locomotor activity and pain perception. TRHR1 distribution on the other hand indicates that this receptor is involved in mediating the endocrine functions of TRH. Replacement or modification of the central histidyl residue of TRH has been shown by the art to severely reduce receptor affinity (Gershengorn and Osman, 1996). Only one exception has been identified that binds with greater affinity than TRH to TRH receptors and that is [3-Me-His$^2$]TRH. Degradation stabilized analogs described in U.S. Pat. Nos. 4,906,614, 5,244,884 and 5,686,420 have all been found to bind to TRH receptor sites within the brain, albeit with less potency than TRH. The art indicates that the structural preferences for ligand binding to TRH receptors and TRH-DE are different (Kelly et al., 2002). For example, both Glp-Asn-ProAMC and Glp-Asn-ProNH$_2$ have been shown to be potent inhibitors of TRH-DE, but display low affinity compared to TRH for [$^3$H][3-Me-His$^2$]TRH-labeled receptors in rat cortical membranes.

The present invention describes novel compounds that potently inhibit TRH-DE and or bind to TRH receptors with high affinity and substantially enhance TRH actions in rat. Potent TRH-DE inhibitors that also bind to TRH receptors and amplify TRH effects have not been previously described and are first in their class. These compounds are distinct from those described in U.S. Pat. Application 20030166944 because they inhibit TRH-DE and or bind to TRH receptor(s). Further, unlike the compounds disclosed herein, the amino acids contained within the structure of TRH-DE inhibitors described in U.S. Pat. Application 20030166944 are all in the L-configuration. Certain compounds of the invention are also different from other compounds that have been shown to bind to TRH receptors with the exception of 3-Me-His$^2$TRH, in that they display greater affinity for TRH receptors than TRH. 3-Me-His$^2$TRH is the only compound described thus far that also binds to TRH receptors with greater affinity than TRH.

OBJECT OF THE INVENTION

One object of the invention is to provide further inhibitors of TRH-DE. Another object of the invention is to provide molecules which mimic the actions of TRH which in turn would lead to a range of pharmaceutical products for use in novel methods of diagnosis, prevention, delaying progression and treatment of disorders in which the effects of TRH would be therapeutically useful, in particular, CNS injury or damage or malfunction. It is a particular object to provide molecules, which bind to TRH receptors with a high affinity, particularly a higher affinity than TRH itself.

SUMMARY OF THE INVENTION

In one aspect the present invention provides compounds of the formula I:

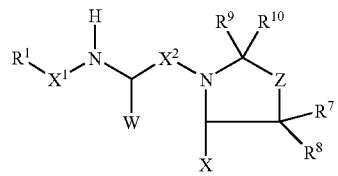

wherein $R^1$ is an optionally substituted 4-, 5- or 6-membered heterocyclic ring having one or more heteroatoms, in which at least one carbon atom of the ring is substituted with O or S or N; $X^1$ is —CO— or —CS— or —CH$_2$CO— or CH($R^4$) wherein $R^4$ is H or optionally substituted alkyl or
—COOH or —COOR$^{11}$ wherein R$^{11}$ is optionally substituted alkyl;

$X^2$ is —CO— or —CS—;

Z is —CH$_2$ or —S— or —O— or —NH—;

$R^7$ and $R^8$ (which may be the same or different) are H, or optionally substituted lower alkyl;

$R^9$ and $R^{10}$ (which may be the same or different) are H, or optionally substituted alkyl, or an optionally substituted carbocyclic ring;

W represents an amino acid residue, natural or un-natural;

X represents 1 to 20 amino acid, at least a majority of which are in the D-configuration, the C-terminal amino acid residue optionally being substituted with an amino group or 7-amino-4-methyl coumarin:

and pharmaceutically acceptable salts thereof.

The invention also provides a compound of claim 1 having the formula Ia

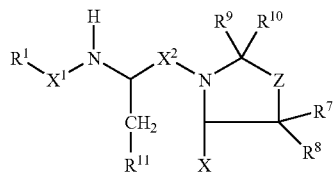

wherein:

$R^1$, $X^1$, $X^2$, Z, $R^7$, $R^8$, $R^9$ and $R^{10}$ are as defined in claim 1;

$R^{11}$ is an imidazole ring or the group;

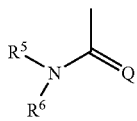

in which Q is O or S; and $R^5$ and $R^6$ (which may be the same or different) are H, or lower alkyl;

and pharmaceutically acceptable salts thereof

Preferred compounds are those in which X may represent 1 to 10 amino acids and particularly preferred are those in which X represents 1 to 3 amino acids. Preferably all of the X amino acids are in the D configuration.

The D-amino acids may be selected from the group consisting of alanine, valine, leucine, isoleucine, proline, phenylalanine, tryptophan, methionine, glycine, serine, threonine, cysteine, tyrosine, asparagine and glutamine. Particularly preferred are phenylalanine, tryptophan and tyrosine.

Amino acids are compounds having the structure $RCHNH_2COOH$. Amino acids can be categorized as neutral, acidic or basic depending on the nature of their specific R group (McMurray). Amino acids may be natural or non-naturally occurring (i.e. un-natural).

In preferred embodiments $R^5$ and $R^6$ are H.

In particular embodiments, $R^5$ and $R^6$ are H and Q is O so that the compounds have asparagine residue (Asn) in the $P_1'$ position. The Asn residue may be in the L-configuration or in the D-configuration. Where Asn is in the D-configuration the molecule does not inhibit TRH degrading ectoenzyme.

W may represent amino acid residues in which the R group is charged or is neutral. W may be selected from the group consisting of asparagine, histidine, leucine, thienylalanine and phenylalanine.

$R^1$ may suitably be:

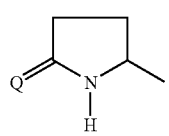 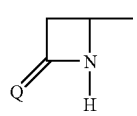 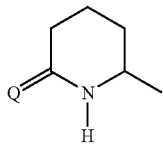

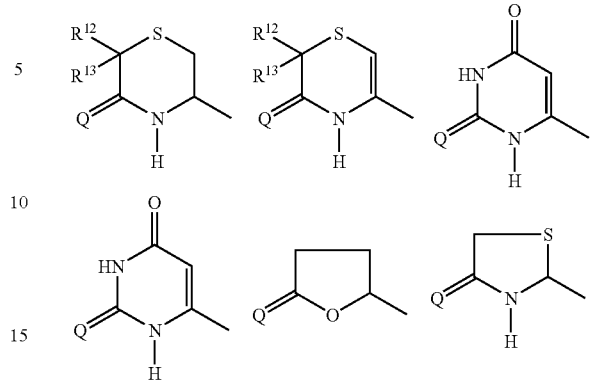

wherein $R^{12}$ is hydrogen, lower alkyl or phenyl, $R^{13}$ is hydrogen or lower alkyl, Q is O or S.

In preferred embodiments, Q is O. Most suitably $R^1$ is a five-membered heterocyclic ring, particularly a pyrrolidinone, thiazolidinone or butyrolactone ring.

In particular preferred embodiments, $R^1$ is

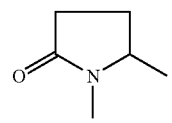

In another aspect the present invention provides a compound having the structure:

Glp-W-Pro-X wherein W represents an amino acid residue, natural or unnatural;

X represents residues of from 1 to 20 amino acids at least a majority of which are in the D-configuration, the C-terminal amino-acid residue optionally being substituted with an amino group or aminomethylcoumarin; and pharmaceutically acceptable salts thereof.

Preferred compounds are those in which X may represent 1 to 10 amino acids and particularly preferred are those in which X represents 1 to 3 amino acids. Preferably all of the X amino acids are in the D configuration.

The D-amino acids may be selected from the group consisting of alanine, valine, leucine, isoleucine, proline, phenylalanine, tryptophan, methionine, glycine, serine, threonine, cysteine, tyrosine, asparagine and glutamine. Particularly preferred are phenylalanine, tryptophan and tyrosine.

The Pro residue may be in the L-configuration or in the D-configuration.

W may represent amino acid residues in which the R group is charged or is neutral. W may be selected from the group consisting of asparagine, histidine, leucine, thienylalanine and phenylalanine.

The Asn residue may be in the L-configuration or in the D-configuration. Where Asn is in the D-configuration the molecule does not inhibit TRH degrading ectoenzyme.

Particularly preferred compounds in accordance with the invention are

Glp-Asn-Pro-D-TyrNH$_2$,
Glp-Asn-Pro-D-TrpNH$_2$,
Glp-Asn-Pro-D-Trp-D-Ser-D-TyrNH$_2$,
Glp-Asn-Pro-D-Trp-D-TyrNH$_2$,
Glp-Asn-Pro-D-Tyr-D-TrpNH$_2$,
Glp-Asn-Pro-D-Tyr-D-Trp-D-TrpNH$_2$
Glp-Asn-Pro-D-Tyr-D-TrpAMC.
Glp-Asn-Pro-D-Trp-D-TyrAMC,
Glp-Asn-Pro-D-Tyr-D-Trp-D-TrpAMC.
Glp-Asn-Pro-D-Phe-D-TyrAMC.
Glp-Asn-Pro-D-Ala-D-TrpAMC.
Glp-Asn-Pro-D-Val-D-Tyr-D-TrpAMC.
Glp-Asn-Pro-D-TrpAMC,
Glp-His-Pro-D-Tyr-D-TrpNH$_2$ and pharmaceutically acceptable salts thereof.

Compounds according to the invention may have substituents present which do not interfere substantially with the function of the compounds as inhibitors of activity of thyrotropin-releasing hormone-degrading ectoenzyme (TRH-DE) or in binding to TRH receptors and acting as TRH mimetics. The substituents may be saturated or unsaturated, branched or unbranched acyclic hydrocarbon groups such as alkyl, alkoxy, alkylene, alkene or alkynyl groups, or saturated or unsaturated, mono- or polycyclic hydrocarbon groups, optionally having heteroatoms in the ring structure and optionally being a fused ring.

In any of the optionally substituted derivatives defined above, suitable substituents may be oxo, thioxo, alkyl, alkenyl, alkynyl, aryl, alkoxy, halo, haloalkyl, nitro, azido, cyano, hydroxyl, hydroxyalkyl, SO$_n$R$^{14}$ where R$^{14}$ is alkyl and n=0, 1 or 2, or a carboxyl or ester group of the formula —COOR$^{15}$ where R$^{15}$ is H or alkyl and which may be in ionic form —COO. Examples of substituents on alkyl groups (including alkyl groups in ring substituents mentioned in the preceding sentence) include halo, nitro or cyano. Optional hetero atoms in the ring(s) include N, O or S. Suitably there may be from 1-3 hetero atoms per ring, and the hetero atoms in any ring may be the same or different.

An alkyl, alkenyl, alkynyl, or alkoxy group may be straight chain or branched and suitably contains from 1 to 20, more suitably from 1 to 10, most suitably from 1 to 5 carbon atoms. A lower alkyl group suitably contains 1 to 5 carbon atoms. Halo includes iodo, bromo, chloro or fluoro. A carbocyclic ring or a mono- or polycyclic ring suitably contains from 4 to 20 ring atoms, more suitably 4 to 8 ring atoms per ring, most suitably in the case of a polycyclic ring a total of 8 to 16 ring atoms, any ring atoms which are not hetero atoms being carbon atoms.

One group of preferred compounds have an N-substituted amide group at the C-terminus of the molecule.

In another aspect the present invention provides compound as defined above and pharmaceutically acceptable salts thereof for use in a method for prevention, delaying progression, or treatment of the human or animal body by therapy or a diagnostic method practiced on the human or animal body.

The invention also provides compounds as defined above and pharmaceutically acceptable salts thereof for use in potentiating or enhancing endogenous TRH and/or in protecting exogenously administered TRH or TRH analogues from degradation by TRH-DE and or acting as a TRH mimetic.

In another aspect the invention also provides agents with dual activities as TRH receptor binding agents and TRH-DE inhibitors comprising compounds as defined above.

The invention also provides a pharmaceutical composition comprising a pharmaceutically effective amount of a compound as defined above, or a pharmaceutically acceptable salt thereof, together with a pharmaceutically acceptable carrier. The composition may further comprise TRH or a TRH analogue.

In another embodiment the compounds of the invention may be administered alone or in combination with other pharmacologically active agents to augment therapeutic efficacy, such as exogenous TRH or TRH analogue(s) and or agents that suppress additional targets, for example, prolyl oligopeptidase.

In a further aspect of the invention the compounds of the invention may be administered in combination with one or more other pharmacologically active substances.

Compounds of the invention may be administered by oral, parenteral, intramuscular (i.m.), intraperitioneal (i.p.), intravenous (i.v.) or subcutaneous (s.c.) injection, nasal, vaginal, rectal or sublingual routes of administration and can be formulated in dosage forms appropriate for each route of administration.

By pharmaceutically effective amount is meant an amount of the compound sufficient to inhibit TRH-DE or to act as a TRH mimetic. Pharmaceutically acceptable carriers are those which may be administered in conjunction with the compounds of the invention without producing deleterious biological effects. Suitable pharmaceutically acceptable carriers are known to those of skill in the art.

The invention may be applied inter alia in the development of therapeutics for any TRH-related disorders, inter alia, brain and spinal injury or tumour, memory loss, spinocerebellar degeneration, pain including spinal cord pain, epilepsy, eating disorders, weight management disorders (particularly obesity), diabetes and CNS related diseases, as well as memory loss, lethargy, anxiety disorders, jet lag, attention deficit disorders, post-traumatic syndrome and as a mood stabilizer or enhancer, to enhance proper fetal development, and as a research tool to investigate TRH and TRH-DE and TRH receptor related cellular processes.

DESCRIPTION OF THE INVENTION

Figure 1:
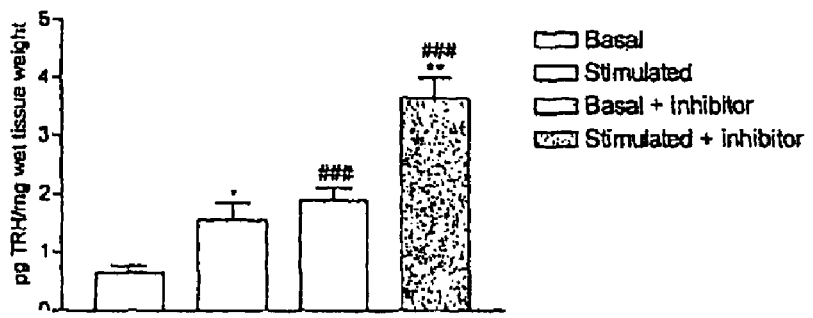
FIG. 1. Release of TRH from rat brain hypothalamic slices under basal and depolarizing conditions in the presence and absence of a TRH-DE inhibitor: (a) Glp-Asn-Pro-AMC (0.1 mM in saline) or (b) Glp-Asn-Pro-Tyr-Trp-Trp-AMC (0.1 mM in DMSO), and (c) Glp-Asn-Pro-D-Tyr-D-TrpNH$_2$ (JAK 4D) (0.1 mM in DMSO). Data are means±s.e.m. of n=6. *p<0.05 p<0.01 *p<0.001 versus corresponding basal; #p<0.05, ###p<0.001 versus corresponding condition in the absence of inhibitor (unpaired, two-tailed Student's t-test).
Figure 1:
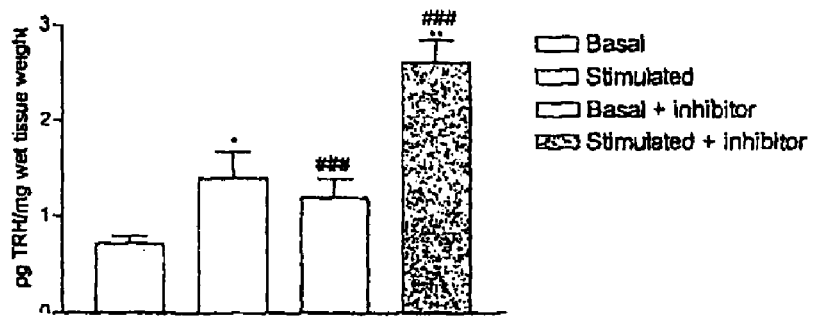
Figure 1:
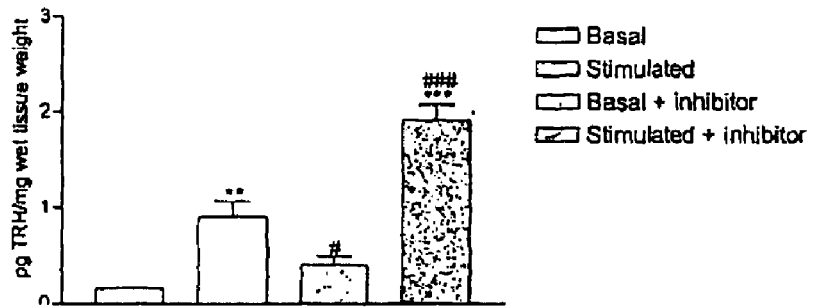

The present invention relates to compounds belonging to the series of compounds disclosed below which inhibit TRH-DE and or have high binding affinity for TRH receptor(s) and act to enhance and or mimic the actions of TRH.

These compounds are distinct from those described in U.S. Pat. Application 20030166944, since they inhibit TRH-DE and/or bind to TRH receptors. Potent TRH-DE inhibitors that also bind to TRH receptors and amplify central effects of TRH are novel and the first in their class. Bi-functional agents, which exert dual actions, may have the potential to produce greater therapeutic benefits. Certain of these compounds are different from other compounds with the exception of 3-Me-His$^2$ TRH, that have been reported by the art to bind to TRH receptors, in that they bind to TRH receptors with greater affinity than TRH. These compounds have not been reported to occur naturally.

The binding capacity offered by in the vicinity of the S2' binding site of TRH-DE was studied. Previous studies had shown that replacement of the C-terminal $NH_2$ group of Glp-Asn-ProNH$_2$ by AMC results in a greater than ten-fold enhancement of binding affinity to TRH-DE. Further luteinizing hormone-releasing hormone (LHRH) binds to the TRH-DE with slightly higher affinity than does TRH (O'Cuinn et al., 1990). TRH and LHRH share the same N-terminal dipeptide sequence, but LHRH is a decapeptide with the primary structure Glp-His-Trp-Ser-Tyr-Gly-Leu-Arg-Pro-GlyNH$_2$ and is not hydrolyzed by TRH-DE (O'Cuinn et al. 1990). Quantitative structure activity studies undertaken for a series of C-terminally extended analogues of Glp-Asn-ProNH$_2$ by means of kinetic assays, using TRH-DE purified from porcine brain as previously described (Kelly et al. 2000a, 2000b, U.S. Pat. App. 20030166944), revealed that C-terminal extension of Glp-Asn-ProNH$_2$ with hydrophobic L-amino acids resulted in a set of TRH-DE inhibitors with nM potency (Table I). The L-amino acids in these peptides were replaced with D-amino acids. The vast majority of naturally occurring polypeptides are composed of L-amino acids and mammalian proteolytic enzymes are designed to work with this stereochemistry. Thus, replacement of L-amino acids by D-amino acids is used in the art in an endeavor to confer stability to proteolytic degradation as described in U.S. Pat. No. 6,703,366. It is recognized by the art that this type of replacement, however, may lead to loss of peptide specificity and or activity as noted by U.S. Pat. No. 4,587,233, Sato et al. 1987 and Fischer 2003, and thus the effect of the replacement is unpredictable. Nevertheless, there are examples in the art where such a replacement has led to compounds with superior biological properties (Leng et al., 1996, Magdolen et al. 2001). Replacement of L-amino acids by D-amino acids has also been used in the art to stabilize bioactive configurations—for example it is known by those skilled in the art that the introduction of D-Pro-Xaa into a polypeptide sequence may stabilized a β-hairpin (Karle et al., 2003). Replacement of L-amino acids by D-amino acids may also be used to scan the relative importance of the stereochemistry of particular functional groups in a peptide structure and also that of local structures within the peptide (Hruby, 2002). In relation to the present invention it has been found that Glp-D-Asn-L-prolineamide is not an effective inhibitor of TRH-DE ($K_i$>1000 mM). In addition, $K_i$ values for Glp-L-Asn-L-prolineamide and Glp-L-Asn-D-prolineamide were found to be 17.5 mM and 31.2 mM, respectively, indicating the enzyme is tolerant to the replacement of L-prolineamide with D-prolineamide. In the examples presented herein it is disclosed that replacement of L-amino acids in the C-terminal extension of Glp-Asn-ProNH$_2$ by D-amino acids was not found to cause any significant changes in affinity for the enzyme.

Unexpectedly, C-terminally extended analogs of Glp-Asn-ProNH$_2$ that contain D-amino acids in the C-terminal extension were found to bind to [$^3$H]-3MeHis-TRH-labelled receptors TRH receptors in rat brain cortex with high affinity. Research shows that [$^3$H][3-Me-His$^2$]TRH binds to a single population of high affinity sites on rat brain cortical membranes with a $K_d$ of around 5 nM (Sharif 1989, Kelly et al., 2002). Since in situ hybridisation studies have revealed that rat brain cortex expresses predominantly TRHR2 it might be speculated that sites labeled by [$^3$H][3-Me-His$^2$]TRH in rat brain cortical membranes correspond to TRHR2. It cannot be ruled out, however, that [$^3$H][3-Me-His$^2$]TRH is binding to a TRH receptor subtype in rat brain cortex that has yet to be identified.

It is not obvious why these compounds bind to both TRH-DE and TRH cortical receptors and this phenomenon could not have been predicted. Previous studies have shown structural preferences for binding to TRH receptors and TRH-DE to be different (Kelly et al., 2002). For example, both Glp-Asn-ProAMC and Glp-Asn-ProNH$_2$ are potent inhibitors of TRH-DE, but display relatively low affinity compared to TRH for [$^3$H]-3MeHis-TRH-labelled receptors in rat cortical membranes. Further, Glp-L-Asn-L-Pro-L-Tyr-L-Trp-L-TrpAMC and Glp-L-Asn-L-Pro-L-Tyr-L-Trp-AMC have also been found to display low affinity for [$^3$H]-3MeHis-TRH-labelled receptors in rat brain cortex. Thus, by extending the structure of Glp-Asn-ProNH$_2$ at the C-terminus with D-amino acids, the inventor has unpredictably significantly altered the properties of TRH-DE inhibitors, disclosed in Kelly et al., 2000a, 2000b and U.S. Pat. Application 20030166944.

With the exception of 3MeHis$^2$-TRH, certain compounds described in the present invention are the only compounds known to bind to TRH receptor(s) with greater affinity than TRH. The art indicates that the side chains of all three amino acids in TRH are involved in TRH receptor binding (Gershengorn and Osman, 1996). Further, only one analog out of hundreds studied has been found to exhibit higher affinity for TRH receptors than TRH; that analog is 3MeHis-TRH. All peptide analogs that have been found to bind to TRH receptors are agonists. To date, no partial agonists or high affinity antagonists of TRH receptors have been identified. Extensive site directed mutagenesis studies and computational modeling have been carried out in relation to TRH receptors, but there is nothing in their teaching to indicate the line of research leading to the present invention of compounds that bind to TRH receptors with greater affinity than does TRH.

The compounds described in the present invention may be administered by oral, parenteral, intramuscular (i.m.), intraperitioneal (i.p.), intravenous (i.v.) or subcutaneous (s.c.) injection, nasal, vaginal, rectal or sublingual routes of administration and can be formulated in dosage forms appropriate for each route of administration. Suitable dosage forms are known to those skilled in the art and are described, for example in U.S. Pat. No. 4,906,614 Giertz et. al. or U.S. Pat.

No. 5,244,884 Spatola et. al. Dosage levels should be sufficient to achieve the TRH-DE inhibiting and TRH mimetic effects required for treatment of the particular physical condition being addressed.

Desirably, the invention will provide for use of a compound of Formula I or Ia or a pharmaceutically acceptable salt thereof in the preparation of a medicament, particularly for the treatment of brain or spinal injuries or other central nervous system disorders or other TRH dependent disorders.

Compounds according to the invention may be administered alone or in combination with further pharmacologically active substances to augment therapeutic efficacy such as exogenous TRH or TRH analogues and or agents directed at additional targets, for example, prolyl oligopeptidase.

Desirably the invention will provide a method of treatment of brain or spinal injuries or other central nervous system disorders or other TRH-dependent disorders, which comprises administering to a patient suffering from such injuries or disorders an amount of a compound of Formula I or Ia or a pharmaceutically acceptable salt thereof effective to potentiate or enhance endogenous TRH and/or protect exogenously administered TRH or TRH analogues from degradation by TRH-DE and or bind to TRH receptors and mimic TRH actions.

According to one aspect, the present invention provides pharmaceutical compositions comprising an effective amount of a compound of Formula I or Ia or a pharmaceutically acceptable salt thereof. Normally the composition will also comprise a pharmaceutically acceptable carrier, particularly an inert carrier.

The term "treat" as used herein is intended to encompass curing as well as ameliorating at least one symptom of the condition or disease. Thus prevention, delaying the progression of a condition or disease and after-care are all included in the definition. Likewise, a "therapeutic" is an agent which cures or ameliorates or prevents at least one symptom of the condition or disease. The invention may be applied in therapy approaches for biologically important disorders affecting certain cell types or cell subpopulations. Similarly the approach may be used to modulate normal and or dysfunctional physiological processes. The invention may also be used in the investigation of the biological mechanisms and cellular processes related to the target TRH-DE and substrates of the target, and or related to the target TRH receptor(s) and ligands thereof, for example, TRH.

EXAMPLES

The examples presented illustrate that compounds of the invention potently inhibit TRH-DE and or bind to TRH receptors with high affinity and elicit and or substantially enhance TRH actions in rat.

General Procedures for Synthesizing Compounds of the Invention:

All reagents were of analytical grade and purchased from Sigma-Aldrich Chemical Company (Ireland) unless stated otherwise. Peptides can be produced using methods familiar to those of ordinary skill in the art. Peptides were synthesized using solution and/or solid phase methods (Walker, 1994) and were purified, analyzed and judged to be homogeneous by HPLC (Kelly et al. 1997, 1999, 2000a, U.S. Pat. App. 20030166944). HPLC analyses were conducted using a Thermo Separation Products Inc. Spectra System HPLC.

Standard solid-phase Fmoc chemistry was employed using the bubbler system under nitrogen gas (Walker, 1994). Rink amide MBHA resin was used for the synthesis of peptide amide sequences, such as Glp-Asn-ProNH$_2$, Glp-Asn-ProD-Tyr-DTrpNH$_2$ and Glp-His-ProDTyr-DTrpNH$_2$. Resins, Fmoc amino acid derivatives and pyroglutamic acid were purchased from Novabiochem (Merck Biosciences Ltd., U.K.). Synthesis of peptide amides was carried out using Rink amide MBHA resin (loading capacity: 0.73 mmol g$^{-1}$). This was swollen using N,N-dimethyl-formamide (DMF) and deprotected with 20% piperidine in DMF for 30 minutes. Each amino acid (3 equivalents (eq.), i.e. 3-fold excess over the resin loading capacity) was coupled to the resin with HBTU/HOBt/DIPEA (3:3:6 eq.) for 1 h. Deprotection of Fmoc was achieved with 20% piperidine in DMF. On completion of peptide assembly, the resin was washed with dichloromethane (DCM), followed by methanol and allowed to dry overnight. The sequence was cleaved from the resin and deprotected by stirring the dry resin in a TFA solution (95%), containing water (2.5%) and triisopropylsilane (2.5%) (10 ml/g dry resin) (v/v/v) at room temperature for 2 h. The reaction mixture was filtered under vacuum and the solvent evaporated under reduced pressure. The residue was washed with petroleum ether and precipitated with diethyl ether. Products obtained following treatment with diethyl ether were purified using a semi preparative C-18 reverse-phase HPLC column (μBondaPak, Waters, USA) and a linear gradient of 0-70% B at a flow rate of 2.5 ml/min (solvent A=0.08% trifluoroacetic acid (TFA) in water; solvent B=40% acetonitrile in 0.08% TFA). Peptide purity was confirmed by analytical HPLC analysis and by mass spectrometry as previously described (Kelly et al. 2000a, U.S. Pat. App. 20030166944).

Peptides with a C-terminal carboxylic acid group e.g. Glp-Asn-ProOH may be synthesized using standard solid phase methods employing for example H-Pro-2-Cl Trityl resin (loading capacity: 0.7 mmol g-1). This resin was swollen using DCM and washed with DMF. Each amino acid (3 eq.) was coupled onto the resin with HBTU/DIPEA (3:6 eq.) at each step. The reaction time at each step was 1 h. Deprotection, cleavage from the resin and precipitation of the product were carried out as described above.

Carboxamides of the invention peptides may be prepared by standard solution phase by coupling to the appropriate amine to a peptide containing a C-terminal carboxylic acid group. For example, carboxamides of Glp-Asn-ProOH may be prepared as follows: to a stirring solution of Glp-Asn-ProOH (0.15 mmol) in DMF (560 ml, 0.26 M), HOBt (1.0 eq.) and DCC (1.0 eq.) were added, followed by the required amine (1.2 eq.). The reaction mixture was stirred at room temperature for 24 h, filtered and the solvent evaporated under reduced pressure. The residue was washed with petroleum ether and precipitated with diethyl ether. The product was purified using HPLC as described above. Peptide purity was confirmed as described earlier.

Glp-Asn-ProNH$_2$, Glp-Asn-Pro-TyrNH$_2$, Glp-Asn-Pro-Trp-Ser-TyrNH$_2$, Glp-Asn-Pro-Trp-TyrNH$_2$, Glp-Asn-Pro-TrpNH$_2$, Glp-Asn-Pro-Tyr-TrpNH$_2$, Glp-Asn-Pro-Tyr-Trp-TrpNH$_2$, Glp-Asn-Pro-AMC Glp-Asn-Pro-Trp-AMC, Glp-Asn-Pro-Trp-Trp-AMC, Glp-Asn-Pro-Tyr-Trp-AMC, Glp-Asn-Pro-Tyr-Trp-Trp-Trp-AMC, Glp-Asn-Pro-D-Tyr-D-TrpNH$_2$, Glp-Asn-Pro-D-Tyr-D-Trp-D-TrpNH$_2$Glp-Asn-Pro-D-Tyr-D-TrpAMC, Glp-Asn-Pro-D-Trp-D-TyrAMC and Glp-Asn-Pro-D-Tyr-D-Trp-D-TrpAMC were custom synthesized either by the American Peptide Company (Sunnyvale, Calif., U.S.A.) or by PolyPeptide Laboratories GmbH (Germany) at the request of the inventor under conditions of confidentiality. TRH and TRH-AMC were purchased from Sigma-Aldrich and Bachem UK Ltd, respectively. The homogeneity and identity of each peptide was confirmed by HPLC and mass spectral analysis. All peptides were stored at −20° C.

Example of Glp-Asn-ProAMC preparation by American Peptide Company 24H27N507 MW 497.5

Peptide Preparation Process:

This peptide was prepared by solution phase chemistry. American Peptide Company provides Boc amino acids and resin. Biograde DCM, DMF and related solvents were obtained from Fisher Scientific. Boc-Pro; Boc-Asn; Glp; BOP and AMC. x g of AMC was dissolved in DMF. The BOP reagent and Boc-Pro were added to the reaction mixture for a period of two hours. Let the reaction react for ~2 hours. Use standard work-up procedure to generate Boc-ProAMC analog. Following removal of Boc group of Boc-ProAMC, Boc-Asn was added along with coupling agent. Boc-Asn-ProAMC was obtained. Repeat same process, Glp was coupled to the sequence. Since no protection was employed, HF cleavage step was avoided. However, if Boc-Asn(Xan) had been used, HF step would have been necessary. After the HF cleavage, extract the ACN/H2O. Crude peptide is purified with RP-HPLC.

Preparative HPLC, Shimadzu 8-LC
Analytical HPLC Shimadzu 10-LC
Analytical column YMC 5 micron C18
Preparative column 3 inch Varian 10 micron C18 RP-HPLC Collect those fraction >95. Dry it over Virtis lyophilizer and white powder was obtained with good yield.

The material was finally tested and released by QC with that parameter specified in COA.

Glp-Asn-ProAMC prepared by this process exhibited the correct molecular weight in Mass Spectral analysis. It had a solubility of 0.5 mg in 0.5 ml water.

RP-HPLC Analysis
Column: 4.6 m i.d.×250: vydac, c18, 5 micron
Others: F:15 ml/min
Buffer A: 0.1% TFA in water Buffer B: 0.1% TFA in CAN
Wavelength . . . 215 . . . nm
C:\CLASS-VP\METHODS\5-35% 20 25.met
Retention Time . . . 13.7 . . . min Derivatives of this type have been previously synthesised by well-known solution solid phase procedures using Boc chemistry (Zimmerman et al. 1977, Fujiwara & Tsuru, 1978). Glp-Asn-ProAMC and other compounds of the invention can be prepared utilising such procedures which are readily understood by those of ordinary skill in the art. As such, the above experimental procedure utilised by APC to provide Glp-Asn-ProAMC herein is only exemplary of suitable methods and this should not be considered to limit the present invention.

The effectiveness of the compounds of the invention to inhibit TRH-DE and or bind to TRH receptor(s) and to elicit and or amplify central TRH effects is described below.

Inhibition of Purified TRH-DE:

The ability of compounds to be hydrolysed by and to inhibit TRH-DE purified from porcine brain was determined using kinetic assays as previously described (Kelly et al. 1999, 2000a, 2000b, U.S. Pat. application 20030166944). $K_i$ values for a series of C-terminally extended analogues of Glp-Asn-Pro$NH_2$ are presented in Table I. Significantly, it can be seen that substantial improvement in potency can be achieved through C-terminal extension of Glp-Asn-ProNH, by L-amino acids. The most potent of the compounds tested was Glp-L-Asn-L-Pro-L-Tyr-L-Trp-L-TrpAMC with a $K_i$ of 1 nM. It can also be seen from Table I that replacement of L-amino acids by D-amino acids in the C-terminal extension did not lead to a significant change in inhibitory potency. [JAK 1, JAK 2, JAK 3, JAK 4 and JAK 5 are described in U.S. Pat. App. No. 20030166944.]

TABLE I $K_i$ values for TRH-DE inhibitors

| I.D | Peptide | $K_i$ (nM) |
| --- | --- | --- |
| JAK 1 | Glp-Asn-Pro-LTyr-LTrp-LTrp-AMC | 1[1] |
| JAK 1D | Glp-Asn-Pro-DTyr-DTrp-DTrpAMC | 30[1] |
| JAK 2 | Glp-Asn-Pro-LTyr-LTrp-AMC | 40 |
| JAK 2D | Glp-Asn-Pro-DTyr-DTrpAMC | 100 |
| JAK 4D 'JAKD' | Glp-Asn-Pro-D-Tyr-D-Trp$NH_2$ | 110 |
| JAK 3 | Glp-Asn-Pro-LTyr-LTrp-LTrp$NH_2$ | 730 |
| JAK 4 | Glp-Asn-Pro-LTyr-LTrp-$NH_2$ | 780 |
| JAK 5 | Glp-Asn-Pro-AMC | 970* |
| JAK 6 | Glp-Asn-Pro$NH_2$ | 16,100* |
| JAK 7D | Glp-His-Pro-D-Tyr-D-Trp$NH_2$ | 19,580 |

HPLC analysis was used, as previously described (Kelly et al. 2000a, U.S. Pat. App. 20030166944), to assess the ability of each compound listed above to act as a TRH-DE substrate. All of the compounds shown above were found to be resistant to TRH-DE hydrolysis. Compounds were then screened for their ability to inhibit TRH-DE purified from porcine brain using fluorometric assays, as previously described (Kelly et al. 2000a, U.S. Pat. App. 20030166944). $K_i$ values were determined either by nonlinear regression analysis of data collected in duplicate at five different substrate concentrations and at least three different concentrations of peptide[1] or were calculated from triplicate determinations of % inhibition using the relationship vi/vo=i=[I]/([I]+Ki (1+[S]/Km)), where vi and vo are the initial rates measured in the presence and absence of inhibitor, respectively, and i, [I], Ki, [S] and Km represent the amount of inhibition, inhibitor concentration, the inhibition constant, the substrate concentration and the Michaelis constant, respectively. *Ki value represents the mean of 11 separate determinations carried out on different days.

TRH-DE Inhibition in Brain Slices:

Increased recovery of a neuropeptide released from brain slices by depolarisation in the presence of a selective peptidase inhibitor is taken by the art to indicate a role for that peptidase in the metabolism of the endogenously released peptide and notably, to indicate the ability of an inhibitor to protect endogenous peptide from degradation in a more physiologically intact environment.

Hypothalamic slices were prepared from rat brain and the ability of TRH-DE inhibitors to protect endogenous TRH from degradation was assessed by measuring the recovery of TRH released from the slices under basal and depolarizing conditions. Hypothalami were rapidly dissected from male Wistar rats (200-250 g) following decapitation and slices (300×300 μm) were cut with a McIlwain tissue chopper. Each incubation contained slices from the hypothalamus of one animal. Slices were initially incubated in a flat-bottomed plastic tube in 0.5 mL $Ca^{2+}$-free Krebs buffer gassed with 95% oxygen/5% carbon dioxide for 10 min in a shaking water bath at 37° C. After 10 min the $Ca^{2+}$-free buffer was replaced by Krebs buffer containing $Ca^{2+}$ (2.5 mM) and incubation was continued for a further 10 min. The tubes were then centrifuged at 2,000 g for 10 min. The resulting supernatant was removed and taken to denote 'basal' release. Subsequently, tissue was incubated at 37° C. for 10 min in buffer containing $Ca^{2+}$ and KCl (50 mM) and the supernatant arising from this incubation was taken to represent 'stimulated' release. TRH-DE inhibitor at a final concentration of 0.1 mM or vehicle (1 mL saline or DMSO) was present throughout the last two incubations. Supernatant samples were frozen at −80° C. until analyzed for TRH content by radioimmunoassay (Lighton et al 1984).

Data presented in FIG. 1 demonstrate that the recovery of TRH released from rat brain slices under basal and depolarizing conditions was significantly increased by the presence of a TRH-DE inhibitor.

Figure 2:
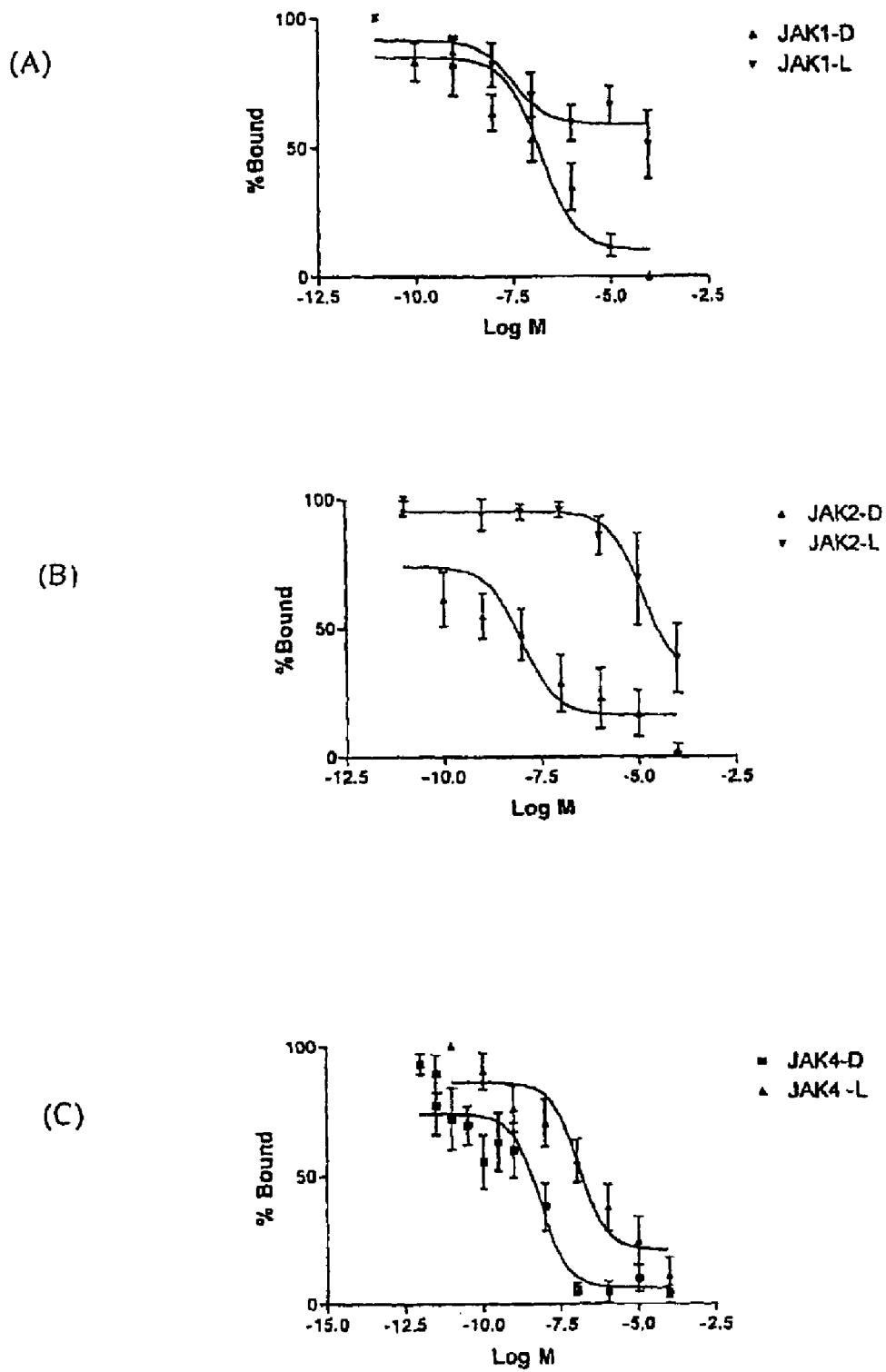
FIG. 2. Displacement of [$^3$H]-3MeHis-TRH by (A) JAK1-D and JAK1-L, (B) JAK2-D and JAK2-L and (C) JAK4-D and JAK4-L. Data are means±SEM, n=3-5.

TRH Receptor Binding:

Radioligand binding assays were carried out to examine the ability of these TRH-DE inhibitors to bind to TRH receptors. This was achieved by measuring the ability of the inhibitors to displace [$^3$H][3-Me-His$^2$]TRH binding to rat cortical membranes. Membranes were prepared from the cortex of male Wistar rats. The binding of [$^3$H]-3MeHis-TRH to TRH receptors in cortical membranes was measured as described previously (Kelly et al., 2002) using 10 mM TRH to define non-specific binding. The affinity of TRH-DE inhibitors for TRH receptors was determined in competition experiments and data were analyzed using GraphPad Prism. The results are summarized in Table II and FIG. 2. Previous studies had shown that both Glp-Asn-ProNH$_2$ (JAK 6) and Glp-Asn-ProAMC (JAK 5) had relatively low affinity compared to TRH for [$^3$H]-3MeHis-TRH-labelled receptors in rat cortical membranes (Kelly et al., 2002). Unexpectedly, the data presented in Table II and FIG. 2 demonstrate that the C-terminally extended analogs Glp-Asn-ProNH$_2$ containing D amino acids are more potent at displacing of [$^3$H]-3MeHis-TRH from native rat cortical TRH receptors than the corresponding analogs containing L amino acids. The rank order of potency of D isomer inhibitors was JAK4-D>JAK2-D>JAK1-D.

TABLE II

Inhibition of [$^3$H]-3MeHis-TRH binding to native rat cortical TRH receptors by TRH analogues. All the JAK compounds were dissolved in DMSO for the purposes of the assay. The Ki value for 3-MeHis-TRH dissolved in DMSO was also determined for comparison.

| Compound | K, M | |
|---|---|---|
| | X is D isomer aa | X is L isomer aa |
| JAK1 | $6.0 \times 10^{-8}$ | $>10^{-4}$ |
| JAK2 | $3.7 \times 10^{-9}$ | $\sim 4 \times 10^{-5}$ |
| JAK4 | $5.5 \times 10^{-9}$ | $1.2 \times 10^{-7}$ |
| TRH | n.d. | $2.2 \times 10^{-8}$ |
| 3-MeHis-TRH (in saline) | n.d. | $1.9 \times 10^{-9}$ |
| 3-MeHis-TRH (in DMSO) | n.d. | $7.4 \times 10^{-8}$ |
| JAK7 | $1.0 \times 10^{-6}$ | n.d. |

The results described above clearly demonstrate that C-terminally extended analogs of Glp-Asn-ProNH$_2$ containing D amino acids in the C-terminal extension bind to [$^3$H]-3Me-His-TRH-labelled receptors in rat brain cortex with greater affinity than TRH, as well as inhibiting TRH-DE with nanomolar potency. Notably JAK 2D and JAK 4D display greater affinity for [$^3$H]-3MeHis-TRH-labelled receptors in rat brain cortex than 3MeHis-TRH.

Pharmacological Effects In Vivo:

The antagonism of barbiturate-induced anesthesia is a well-recognized pharmacological effect of TRH and is used in the art to indicate successful central delivery and activity of TRH analogues.

The ability of Glp-Asn-Pro-D-Tyr-D-TrpNH$_2$ to elicit this analeptic effect of TRH was assessed and compare to that of TRH. Male Wistar rats (150-250 g) were anaesthetized with sodium pentobarbitone (30 mg/kg i.p.). After 10 mins, TRH (1 mg/kg) or Glp-Asn-Pro-D-Tyr-D-TrpNH$_2$ (1 mg/kg) were administered i.v. Animals were placed on their backs and sleep times recorded. From Table III it can be seen that both Glp-Asn-Pro-D-Tyr-D-TrpNH$_2$ and TRH significantly ($p<0.05$, Student's t-test) reduce barbiturate-induced sleep time in rats.

TABLE III

Effects of TRH and JAK 4D on barbiturate-induced sleep time.

| Treatment | Sleep time (min) | n |
|---|---|---|
| Control | $70.9 \pm 5.1$ | 16 |
| TRH 1 mg/kg | $54.5 \pm 4.3$* | 13 |
| JAK4D 1 mg/kg | $54.1 \pm 2.4$** | 6 |

Data are means ± SEM of n = 6-16 experiments.
*$p < 0.05$,
**$p < 0.001$ vs control (Student's t-test). This analeptic effect was measured by determining the ability of the test peptides to reduce barbiturate-induced narcosis. Male Wistar rats (150-250 g) were anaesthetized with sodium pentobarbitone (30 mg/kg i.p.). After 10 mins, the test peptide was administered i.v. Animals were placed on their backs and sleep times recorded.

Behavioural Effects:

TRH has been shown to produce several distinctive behavioral responses when administered to rats by peripheral or central injection. These include, increased locomotor activity (21-22), induction of blinking and forepaw licking and body shaking behavior, often referred to as 'wet dog shakes' (WDS) Kelly et al., 2000b). Previously JAK and colleagues have shown that Glp-Asn-ProNH$_2$ and JAK 5 can amplify these central effects of TRH in vivo (Kelly et al., 2000b). As mentioned above, both of these TRH-DE inhibitors were found to have low affinity compared to TRH for [$^3$H]-3Me-His-TRH-labelled receptors in rat cortical membranes, supporting the interpretation that inhibition of TRH-DE underpins their observed behavioral effects.

The effects of TRH and the TRH-DE inhibitors on rat behavior were measured as previously described (Kelly et al., 2000b). Male Wistar rats (150-250 g) were placed in individual perspex boxes and allowed to acclimatize for 20 min. The rats were then administered vehicle or inhibitor (0.1-10 mg/kg i.p., as indicated), followed 15 min later by a second treatment with either vehicle or TRH (1-20 mg/kg i.p, as indicated). Individual behaviors were recorded for 30 sec at 5 min intervals by an observer who was blind to treatment. Behaviors during each observation period were summed to yield a total activity score.

Figure 3:
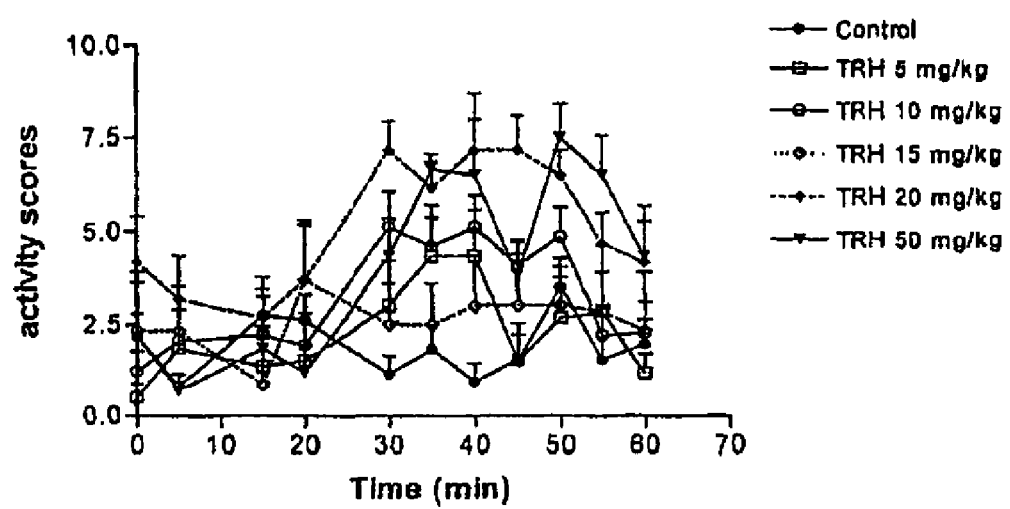
FIG. 3. Effect of TRH on rat activity scores. TRH was administered at t=25 min. Points are means±SEM, n=5-21.

TRH (5-50 mg/kg) caused a dose-dependent increase in activity (FIG. 3) ($p<0.001$ ANOVA). Behavioral responses to 20 and 50 mg/kg TRH were similar indicating that a ceiling effect may have been reached.

Figure 4:
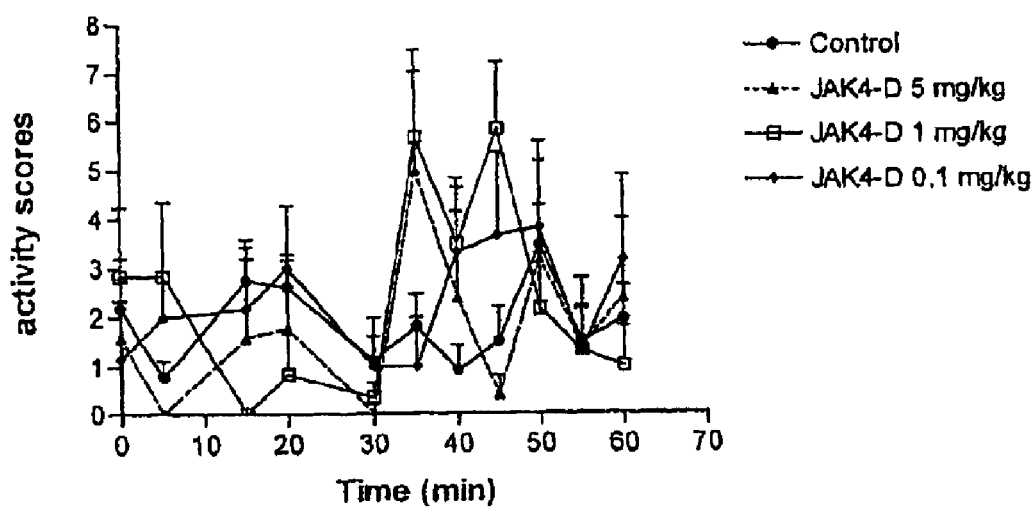
FIG. 4. Effect of JAK4-D on spontaneous activity of rats. JAK4-D was administered at t=10 min. Points are means±SEM, n=5-21
Figure 5:
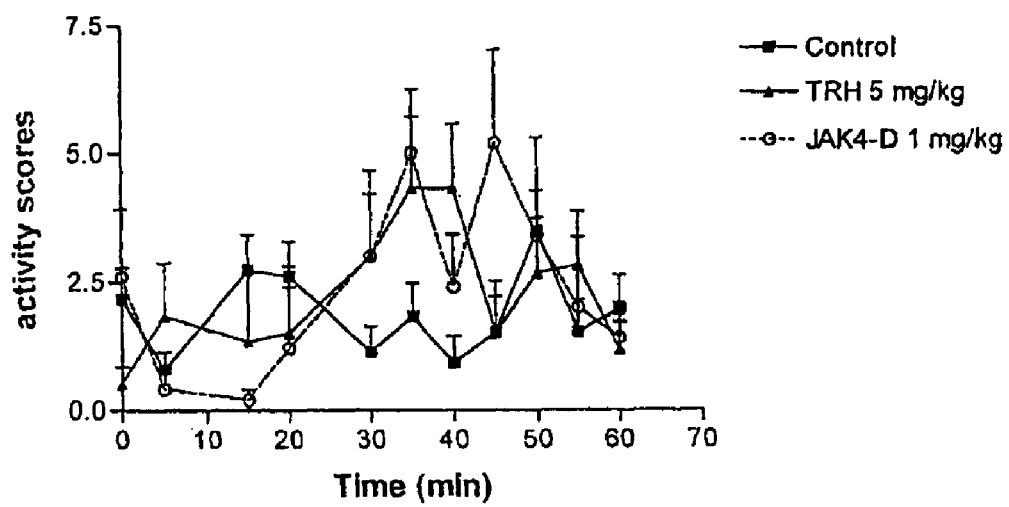
FIG. 5. Comparison of the effects of JAK4-D 1 mg/kg and TRH 5/mg/kg on spontaneous activity of rats. JAK4-D was administered at t=10 min; TRH was administered at t=25 min. Points are means±SEM, n=5-21
Figure 6:
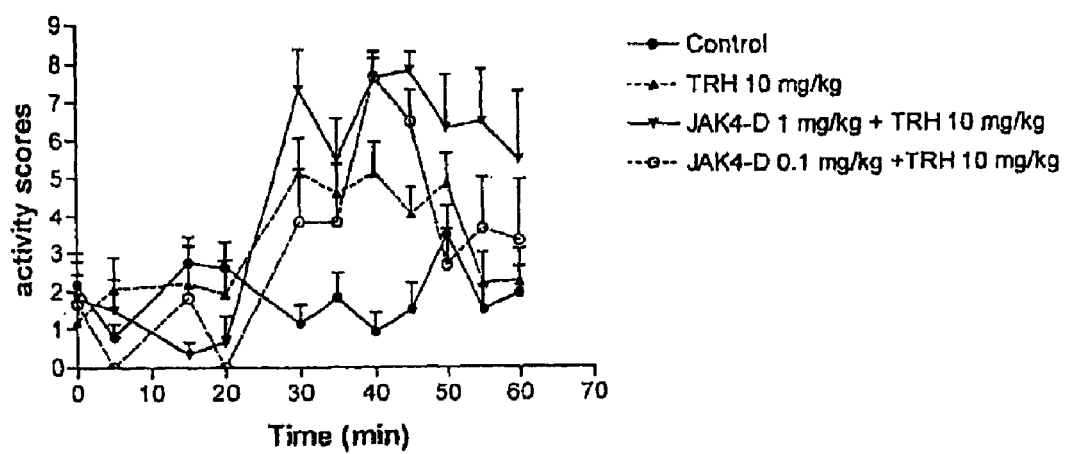
FIG. 6. Effect of JAK4-D on the stimulation of rat activity by 10 mg/kg TRH. JAK4-D was administered at t=10 min; TRH was administered at t=25 min. Points are means±SEM, n=5-21

It can be seen that JAK4-D (0.1-5 mg/kg) causes a transient increase in spontaneous rat activity scores in comparison with vehicle treated controls. This was statistically significant for 0.1 mg/kg JAK4-D over the period 40-45 min and for 1 mg/kg JAK4-D over the period 35-45 min ($p<0.05$ and $p<0.001$ respectively, two-way ANOVA) (FIG. 4). The response produced by 1 mg/kg JAK4-D was comparable to that produced by TRH 5 mg/kg (FIG. 5). Pre-treatment of rats with 0.1 mg/kg JAK4-D enhanced the stimulatory effect of 10 mg/kg TRH 15-20 min after administration of TRH ($p<0.05$ vs TRH alone, two-way ANOVA). 1 mg/kg JAK4-D enhanced and prolonged responses to TRH over the entire observation period ($p<0.0001$ vs TRH, two-way ANOVA) (FIG. 6). It is notable that co-administration of 0.1 mg/kg JAK4D with 10 mg/kg TRH caused responses equivalent to those achieved by 20 and 50 mg/kg TRH.

Figure 7:
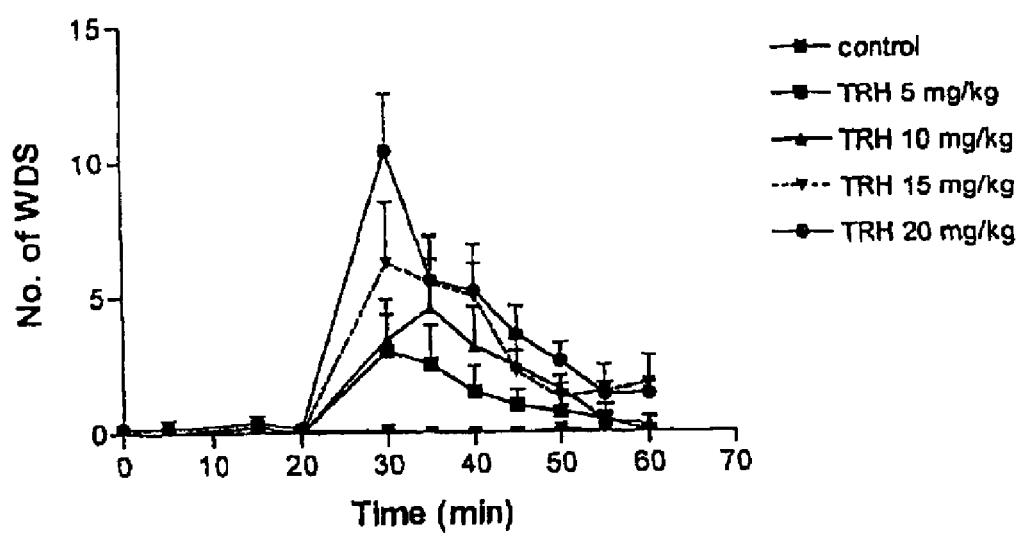
FIG. 7. Stimulation of wet dog shakes (WDS) by TRH. TRH was administered at t=25 min. Points are means±SEM, n=6

The effects of TRH and TRH-DE inhibitors on wet dog shaking (WDS) behavior were measured as follows: male Wistar rats (150-250 g) were placed in individual perspex boxes and allowed to acclimatize for 20 min. They were then administered vehicle or inhibitor (0.1-10 mg/kg i.p., as indicated), followed 15 min later by a second treatment with either vehicle or TRH (1-20 mg/kg i.p., as indicated). Animals were videotaped and the tapes were subsequently evaluated for the number of WDS that occurred during 5 min observation periods. TRH was found to cause a concentration-dependent increase in WDS. Maximum numbers of WDS were recorded 5 min post administration of TRH and the effects of TRH persisted for approximately 20 min (FIG. 7).

Figure 8:
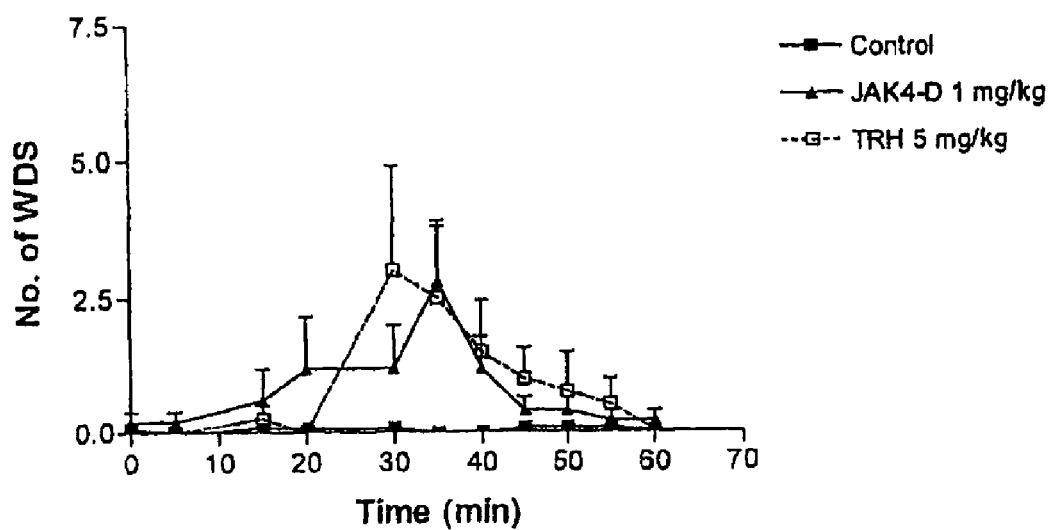
FIG. 8. Effect of JAK4-D on wet dog shaking (WDS) behavior in rats. JAK4-D was administered at t=10 min; TRH was administered at t=25 min. Points are means±SEM, n=4-6
Figure 9:
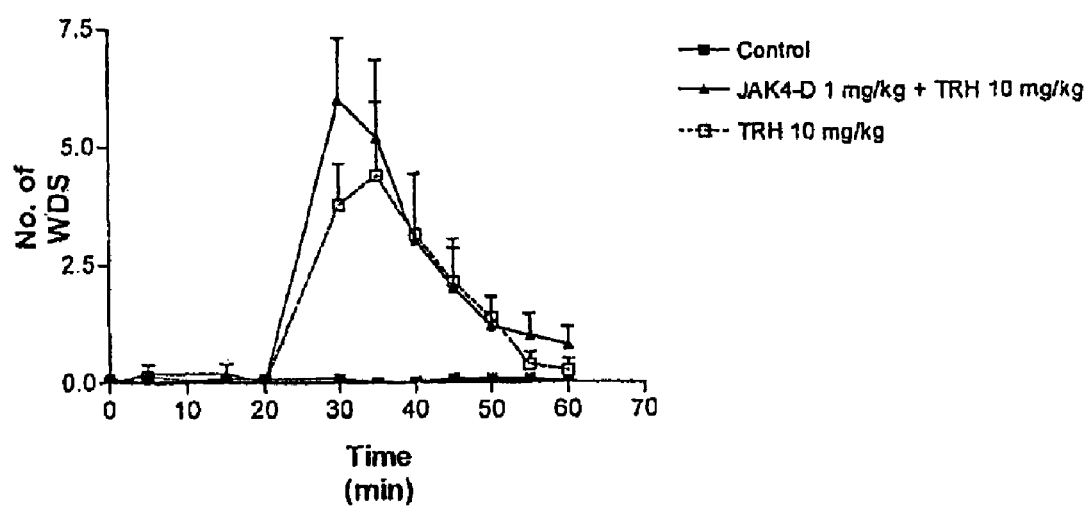
FIG. 9. Effect of JAK4-D on TRH-induced wet dog shakes (WDS). JAK4-D was administered at t=10 min; TRH was administered at t=25 min. Points are means±SEM, n=4-6

1 mg/kg JAK4-D increased the occurrence of WDS to a level that was comparable with the response produced by 5 mg/kg TRH (FIG. 8). Furthermore, pre-treatment with 1 mg/kg JAK4-D enhanced the peak WDS response to 10 mg/kg TRH (p<0.01, t-test) (FIG. 9).

Crystallographic Analysis

Crystals of Glp-Asn-Pro-DTyr-DTrpNH$_2$ (JAK4D) were grown from a mixture of DMSO (15% v/v) and saline. Data from x-ray crystallographic analysis is consistent with and confirms the stereochemistry of the synthesized peptide and that the compound is enantiomerically pure. The absolute structure was confirmed by examination of Flack×parameter.

Structure of Glp-Asn-Pro-DTyr-DTrpNH$_2$ (JAK4D) as determined by single crystal analysis:

TABLE 1

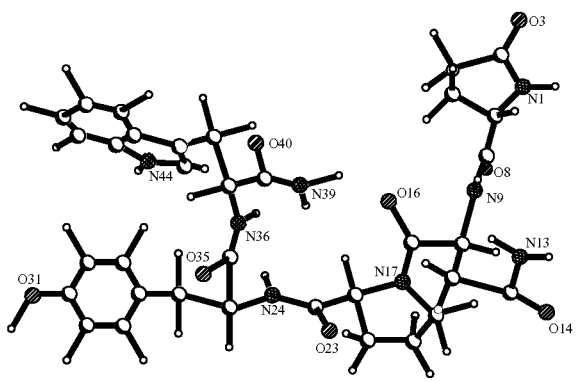

Crystal data and structure refinement for
L-Glp-L-Asn-L-Pro-D-Tyr-D-TrpNH$_2$

| | |
|---|---|
| Identification code | L-Glp-L-Asn-L-Pro-D-Tyr-D-TrpNH$_2$ |
| Empirical formula | C$_{38}$H$_{58}$N$_8$O$_{13}$S$_2$ |
| Formula weight | 899.04 |
| Temperature | 153(2) K. |
| Wavelength | 0.71073 Å |
| Crystal system | Monoclinic |
| Space group | P2(1) |
| Unit cell dimensions | a = 12.4656(7) Å   α = 90°. |
| | b = 11.2767(7) Å   β = 90.9110(10)°. |
| | c = 15.6497(9) Å   γ = 90°. |
| Volume | 2199.6(2) Å$^3$ |
| Z | 2 |
| Density (calculated) | 1.357 Mg/m$^3$ |
| Absorption coefficient | 0.192 mm$^{-1}$ |
| F(000) | 956 |
| Crystal size | 0.45 × 0.41 × 0.24 mm$^3$ |
| Theta range for data collection | 1.63 to 27.50°. |
| Index ranges | −16 <= h <= 16, |
| | −14 <= k <= 14, −18 <= l <= 20 |
| Reflections collected | 21457 |
| Independent reflections | 10060 [R(int) = 0.0248] |
| Completeness to theta = 27.50° | 99.9% |

TABLE 1-continued

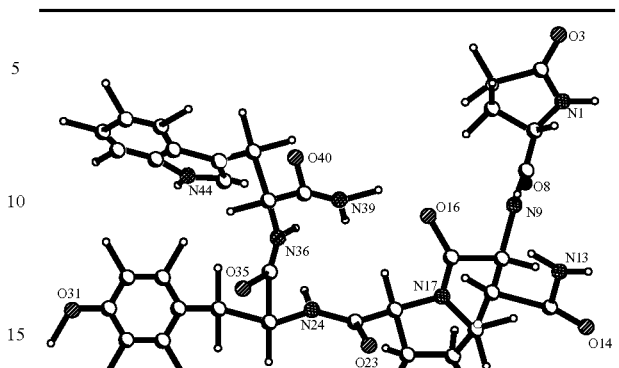

Crystal data and structure refinement for
L-Glp-L-Asn-L-Pro-D-Tyr-D-TrpNH$_2$

| | |
|---|---|
| Absorption correction | Semi-empirical from equivalents |
| Max. and min. transmission | 0.9553 and 0.8099 |
| Refinement method | Full-matrix least-squares on F$^2$ |
| Data/restraints/parameters | 10060/3/568 |
| Goodness-of-fit on F$^2$ | 1.046 |
| Final R indices [I >2sigma(I)] | R1 = 0.0547, wR2 = 0.1423 |
| R indices (all data) | R1 = 0.0600, wR2 = 0.1474 |
| Absolute structure parameter | −0.01(7) |
| Largest diff. peak and hole | 0.888 and −0.449 e.Å$^{-3}$ |

TABLE 2

Atomic coordinates (×10$^4$) and equivalent isotropic displacement parameters (Å$^2$ × 10$^3$) for L-Glp-L-Asn-L-Pro-D-Tyr-D-TrpNH$_2$. U(eq) is defined as one third of the trace of the orthogonalized U$^{ij}$ tensor.

| | x | y | z | U(eq) |
|---|---|---|---|---|
| N(1) | −691(2) | 9195(2) | 4355(1) | 23(1) |
| C(2) | 30(2) | 10055(2) | 4386(2) | 25(1) |
| O(3) | 124(2) | 10856(2) | 3841(1) | 31(1) |
| C(4) | 692(2) | 9930(3) | 5199(2) | 32(1) |
| C(5) | 464(2) | 8670(3) | 5491(2) | 33(1) |
| C(6) | −640(2) | 8383(2) | 5072(2) | 24(1) |
| C(7) | −1536(2) | 8582(2) | 5704(2) | 20(1) |
| O(8) | −1991(2) | 9535(2) | 5779(1) | 27(1) |
| N(9) | −1748(2) | 7618(2) | 6181(1) | 20(1) |
| C(10) | −2482(2) | 7697(2) | 6888(2) | 20(1) |
| C(11) | −2635(2) | 6462(2) | 7279(2) | 25(1) |
| C(12) | −3238(2) | 5659(2) | 6647(2) | 27(1) |
| N(13) | −2709(2) | 4703(2) | 6380(2) | 33(1) |
| O(14) | −4135(2) | 5924(2) | 6409(2) | 43(1) |
| C(15) | −2046(2) | 8526(2) | 7586(2) | 17(1) |
| O(16) | −1070(1) | 8655(2) | 7690(1) | 22(1) |
| N(17) | −2763(2) | 9020(2) | 8094(1) | 17(1) |
| C(18) | −3945(2) | 9016(2) | 8013(2) | 23(1) |
| C(19) | −4272(2) | 10045(2) | 8578(2) | 22(1) |
| C(20) | −3441(2) | 10020(2) | 9306(2) | 24(1) |
| C(21) | −2394(2) | 9605(2) | 8878(2) | 16(1) |
| C(22) | −1794(2) | 8699(2) | 9433(1) | 16(1) |
| O(23) | −2001(2) | 7637(2) | 9402(2) | 25(1) |
| N(24) | −1046(2) | 9143(2) | 9974(1) | 15(1) |
| C(25) | −460(2) | 8358(2) | 10552(1) | 15(1) |
| C(26) | 125(2) | 9114(2) | 11240(2) | 20(1) |
| C(27) | 875(2) | 8397(2) | 11805(2) | 18(1) |
| C(28) | 509(2) | 7755(2) | 12498(2) | 23(1) |
| C(29) | 1200(2) | 7032(2) | 12972(2) | 24(1) |
| C(30) | 2270(2) | 6942(2) | 12760(2) | 19(1) |
| O(31) | 2979(2) | 6234(2) | 13196(1) | 26(1) |
| C(32) | 2653(2) | 7609(2) | 12082(2) | 22(1) |
| C(33) | 1960(2) | 8326(2) | 11615(2) | 20(1) |
| C(34) | 331(2) | 7565(2) | 10081(1) | 15(1) |
| O(35) | 496(1) | 6542(2) | 10348(1) | 20(1) |
| N(36) | 873(2) | 8036(2) | 9433(1) | 16(1) |

TABLE 2-continued

Atomic coordinates (×10⁴) and equivalent isotropic displacement parameters ($Å^2 \times 10^3$) for L-Glp-L-Asn-L-Pro-D-Tyr-D-TrpNH₂. U(eq) is defined as one third of the trace of the orthogonalized $U^{ij}$ tensor.

| | x | y | z | U(eq) |
|---|---|---|---|---|
| C(37) | 1793(2) | 7424(2) | 9070(2) | 17(1) |
| C(38) | 1541(2) | 6631(2) | 8295(2) | 19(1) |
| N(39) | 666(2) | 6866(2) | 7835(1) | 23(1) |
| O(40) | 2181(2) | 5850(2) | 8127(1) | 31(1) |
| C(41) | 2657(2) | 8327(2) | 8795(2) | 19(1) |
| C(42) | 3086(2) | 9096(2) | 9508(2) | 19(1) |
| C(43) | 2729(2) | 10199(2) | 9710(2) | 21(1) |
| N(44) | 3306(2) | 10650(2) | 10392(1) | 23(1) |
| C(45) | 4070(2) | 9828(2) | 10635(2) | 20(1) |
| C(46) | 4859(2) | 9884(3) | 11283(2) | 26(1) |
| C(47) | 5530(2) | 8916(3) | 11381(2) | 28(1) |
| C(48) | 5422(2) | 7915(3) | 10853(2) | 29(1) |
| C(49) | 4648(2) | 7861(2) | 10208(2) | 23(1) |
| C(50) | 3953(2) | 8834(2) | 10091(2) | 19(1) |
| S(60) | 3903(1) | 7583(1) | 5607(1) | 40(1) |
| C(61) | 3645(4) | 7810(4) | 6708(2) | 58(1) |
| C(62) | 3448(4) | 6082(4) | 5543(3) | 61(1) |
| O(63) | 3110(2) | 8321(3) | 5115(2) | 56(1) |
| S(70) | 5519(1) | 6343(1) | 3738(1) | 45(1) |
| C(71) | 6628(3) | 6557(5) | 4451(3) | 60(1) |
| C(72) | 5229(3) | 7870(4) | 3526(2) | 47(1) |
| O(73) | 5969(2) | 5829(3) | 2935(2) | 57(1) |
| O(80) | 9498(2) | 5198(2) | 1608(1) | 23(1) |
| O(81) | 2178(2) | 3951(2) | 6998(1) | 29(1) |
| O(82) | 2168(3) | 1732(3) | 7721(2) | 63(1) |

REFERENCES

Charli, J.-L., Mendez, M., Vargas, M.-A., Cisneros, M., Assai, M., Joseph-Bravo, P., and Wilk, S. (1989) Neuropeptides 14, 191-196

Faden A. I., & Salzman, S. (1992) Trends Pharmacol Sci. 13, 29-35

Fischer, P. M. (2003) Curr. Protein Pept. Sci. 4, 339-356

Fujiwara K. and Tsuru D., J. Biochem. (1978) 83, 1145-1149

Gershengorn M C, Osman R. (1996) Physiol Rev. 76(1), 175-91

Horita, A. (1998) Life Sci. 62, 1443-1448

Hruby V J. (2000) Nat Rev Drug Discov. 1(11), 847-58

Karle, I. L., Gopi, H. N., and Balaram, P. (2003) PNAS 100, 13946-13951

Kelly J A. (1995) Essays Biochem. 30, 133-49

Kelly J A, Slator G R, Tipton K F, Williams C H, Bauer K. (1999) Anal Biochem. 274(2), 195-202

Kelly J A, Slator G R, Tipton K F, Williams C H, Bauer K. (2000a) J. Biol. Chem. 275(22), 16746-51

Kelly J A, Bennett G W, Beckett S, Slator G R, Roe C H, O'Loinsigh E D, and O'Boyle K M. (2000b) Br. J. Pharmacol. 133, 187P Kelly, J. A., Slator, G. R., O'Boyle, K. M. (2002) Biochem. Pharmacol. 63, 2197-2206

Leng, N., Grasso P. and Reichert L. E. Jr. (1996) Pept. Res. 9, 188-194

Lighton, C., Marsden, C. A., and Bennett, G. W. (1984) Neuropharmacology 23, 55-60

Luo L., Yano N, Mao Q, Jackson I M, Stopa E G. (2002) J Alzheimers Dis. 4(2), 97-103

Magdolen, V., Burgle, M., de Prada, N. A., Schmiedeberg, N., Reimer, C., Schroeck, F., Kellerman, J., Degitz, K., Wilhelm, O. G., Schmitt, M., and Kessler, H. (2001) Biol. Chem. 382, 1197-1205

McMurry, J. (1984) Organic Chemistry Brooks/Cole Publishing Company U.S.A.

O'Cuinn, G., O'Connor, B., and Elmore, M. (1990) J. Neurochem. 54, 1-13

Pascual, I., Gil-Parrado, S., Cisneros, M., Joseph-Bravo, P., Diaz, J., Possani, L. D., Charli, J. L., and Chavez, M. (2004) Int. J. Biochem. Cell Biol. 36, 138-152

Sato, K., Hotta, M., Kageyama, J., Chaing, T. C., Hu, H. Y., Dong, M. H., and Ling, N. (1987) Biochem. Biophys. Res. Commun. 149, 531-537

Schechter, I., and Berger, A. (1967) Biochem. Biophys. Res Commun. 27, 157-162

Sharif N A (1989) Ann. NY Acad. Sci. 553, 147-175

Walker, B. (1994) In Synthetic Antigens: A Practical Approach (Wisdom, G. B., ed) pp. 27-81, Oxford University Press, Oxford, U.K Zimmerman M. Ashe B., Yurewicz E. C. and Patel G., (1977) Anal. Biochem. 78, 47-51

The invention claimed is:

1. A compounds of Formula I:

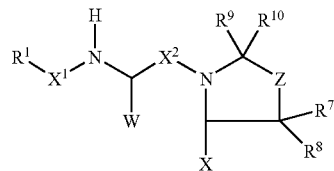

wherein $R^1$ is an optionally substituted 4-, 5- or 6-membered heterocyclic ring comprising one or more heteroatoms, in which at least one carbon atom of the ring is substituted with O or S or N;

$X^1$ is —CO— or —CS— or —CH₂CO— or CH($R^4$), wherein $R^4$ is H, or an optionally substituted alkyl, or a —COOH or —COO$R^{11}$, wherein $R^{11}$ is an optionally substituted alkyl;

$X^2$ is —CO— or —CS—;

Z is —CH₂— or —S— or —O— or —NH—;

$R^7$ and $R^8$ are each independently H or an optionally substituted lower alkyl;

$R^9$ and $R^{10}$ are each independently H, an optionally substituted alkyl, or an optionally substituted carbocyclic ring;

W represents an amino acid residue;

X represents a 1 to 20 amino acid, at least a majority of which are in the D-configuration, the C-terminal amino acid residue optionally being substituted with an amino group or 7-amino-4-methyl coumarin;

and pharmaceutically acceptable salts thereof.

2. The compound of claim 1 having the formula Ia wherein:

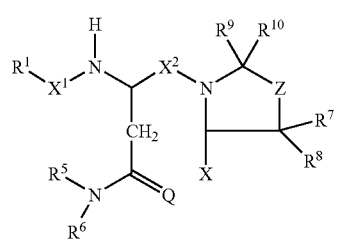

$R^1$, $X^1$, $X^2$, Z, $R^7$, $R^8$, $R^9$ and $R^{10}$ are as defined in claim 1; in which Q is O or S; and $R^5$ and $R^6$ are each independently H or lower alkyl; and pharmaceutically acceptable salts thereof.

3. The compound of claim 1, wherein all of the X amino acids are in the D configuration.

4. The compound of claim 1, wherein X is an amino acid residue in which the R group is neutral.

5. The compound of claim 4, wherein W is a the amino acid is a naturally occurring amino acid.

6. The compound of claim 1, wherein W represents the side chain of an amino acid residue in which the R group is neutral or charged.

7. The compound of claim 1, wherein W is asparagine in the D-configuration.

8. The compound of claim 1, wherein Z is —CH$_2$— and $R^7$ and $R^8$ are H.

9. The compound of claim 8, wherein $R^9$ and $R^{10}$ are H to give Pro in the P$_2$' position, and Pro is in the D- or L-configuration.

10. The compound of claim 1, wherein $X^1$ and $X^2$ are —CO—.

11. The compound of claim 1, wherein $R^1$ is selected from the group consisting of:

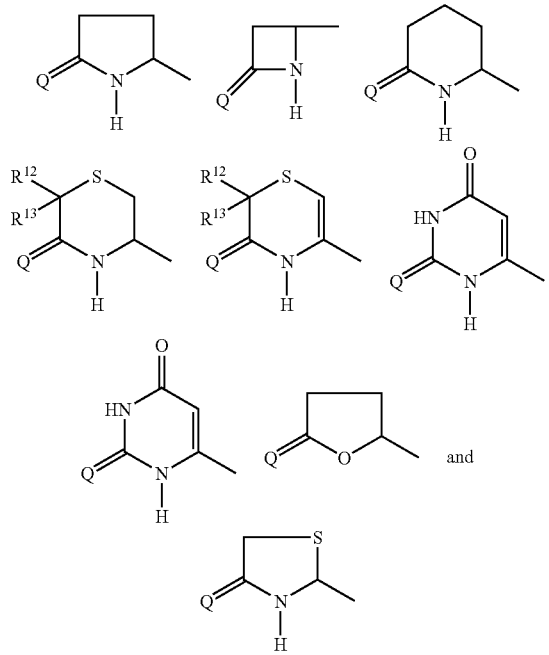

and wherein $R^{12}$ is a hydrogen, a lower alkyl or a phenyl;
$R^{13}$ is a hydrogen or a lower alkyl; and
Q is O or S.

12. The compound of claim 11, wherein Q is O.

13. The compound of claim 1, wherein $R^1$ is a five-membered pyrrolidinone, thiazolidinone or butyrolactone ring.

14. A compound having the structure:

Glp-W-Pro-X wherein W represents an amino acid residue;
X represents residues of from 1 to 20 amino acids at least a majority of which are in the D-configuration, the C-terminal amino-acid residue optionally being substituted with an amino group or aminomethylcoumarin;
and pharmaceutically acceptable salts thereof.

15. The compound of claim 14, wherein X is an amino acid residue comprising neutral side chains.

16. The compound of claim 14, wherein all the X residues are in the D-configuration.

17. The compound of claim 14, wherein W is a naturally occurring amino acid.

18. The compound of claim 14, wherein the W is a neutral or charged amino acid residue.

19. The compound of claim 14, wherein W is asparagine in the D-configuration.

20. The compound of claim 14, wherein the compound is selected from the group consisting of:
Glp-Asn-Pro-D-TyrNH$_2$;
Glp-Asn-Pro-D-TrpNH$_2$;
Glp-Asn-Pro-D-Trp-D-Ser-D-TyrNH$_2$:
Glp-Asn-Pro-D-Trp-D-TyrNH$_2$;
Glp-Asn-Pro-D-Tyr-D-TrpNH$_2$;
Glp-Asn-Pro-D-Tyr-D-Trp-D-TrpNH$_2$;
Glp-Asn-Pro-D-Tyr-D-TrpAMC;
Glp-Asn-Pro-D-Trp-D-TyrAMC;
Glp-Asn-Pro-D-Tyr-D-Trp-D-TrpAMC;
Glp-Asn-Pro-D-Phe-D-TyrAMC;
Glp-Asn-Pro-D-Ala-D-TrpAMC;
Glp-Asn-Pro-D-Val-D-Tyr-D-TrpAMC;
Glp-Asn-Pro-D-TrpAMC; and
Glp-His-Pro-D-Tyr-D-TrpNH$_2$;
and pharmaceutically acceptable salts thereof.

21. A pharmaceutical composition comprising a pharmaceutically effective amount of a compound as defined in claim 1 or claim 14, or a pharmaceutically acceptable salt thereof, together with a pharmaceutically acceptable carrier.

22. The pharmaceutical composition of claim 21, further comprising thyrotropin-releasing hormone (TRH) or a TRH analogue.

23. A method of modulating a thyrotropin-releasing hormone (TRH) action by administering an effective amount of a compound as defined in claim 1 or claim 14 or a pharmaceutically acceptable salt thereof, as a TRH mimetic or TRH receptor ligand.

* * * * *

UNITED STATES PATENT AND TRADEMARK OFFICE
CERTIFICATE OF CORRECTION

PATENT NO. : 7,713,935 B2
APPLICATION NO. : 11/576228
DATED : May 11, 2010
INVENTOR(S) : Kelly Page 1 of 1

It is certified that error appears in the above-identified patent and that said Letters Patent is hereby corrected as shown below:

In claim 1, column 22, line 21, delete "A compounds" and insert --A compound-- therefor.

In claim 5, column 23, line 7, delete "is a the amino acid".

Signed and Sealed this

Tenth Day of August, 2010

David J. Kappos
*Director of the United States Patent and Trademark Office*